United States Patent
Shaffer

(10) Patent No.: US 9,759,670 B2
(45) Date of Patent: Sep. 12, 2017

(54) BORE IMAGING SYSTEM

(71) Applicant: Mitutoyo Corporation, Kanagawa-ken (JP)

(72) Inventor: Jamie Lyn Shaffer, Bothell, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 476 days.

(21) Appl. No.: 14/581,926

(22) Filed: Dec. 23, 2014

(65) Prior Publication Data

US 2016/0178534 A1 Jun. 23, 2016

(51) Int. Cl.
G01V 3/00 (2006.01)
G01N 21/954 (2006.01)
G01M 15/02 (2006.01)

(52) U.S. Cl.
CPC .......... *G01N 21/954* (2013.01); *G01M 15/02* (2013.01); *G01N 2021/9542* (2013.01)

(58) Field of Classification Search
USPC ........................................................ 324/318
See application file for complete search history.

(56) References Cited

U.S. PATENT DOCUMENTS

| | | | | |
|---|---|---|---|---|
| 4,674,834 A * | 6/1987 | Margolin | ................. | G02B 6/06 250/227.2 |
| 4,760,421 A * | 7/1988 | Margolin | ................. | G02B 6/06 250/227.2 |
| 4,762,391 A * | 8/1988 | Margolin | ................. | G02B 6/06 250/227.2 |
| 4,849,626 A | 7/1989 | Franklin, Jr. | | |
| 5,327,514 A * | 7/1994 | Dujon | ...................... | G02B 6/06 348/E5.028 |
| 5,515,470 A * | 5/1996 | Eikelmann | ............... | G02B 6/04 250/227.2 |
| 5,930,433 A * | 7/1999 | Williamson | ............. | G02B 6/06 356/444 |
| 6,743,337 B1 * | 6/2004 | Ischdonat | ............ | D21G 9/0009 162/198 |
| 6,791,072 B1 | 9/2004 | Prabhu | | |
| 6,849,843 B2 | 2/2005 | Ansorge et al. | | |
| 7,636,204 B1 | 12/2009 | Bourget | | |
| 7,786,421 B2 | 8/2010 | Nikzad et al. | | |
| 8,334,971 B2 | 12/2012 | Keller et al. | | |
| 8,372,726 B2 | 2/2013 | de Graff et al. | | |
| 8,570,505 B2 | 10/2013 | Baleine et al. | | |
| 8,742,325 B1 * | 6/2014 | Droz | ..................... | G01J 1/0448 250/239 |

(Continued)

FOREIGN PATENT DOCUMENTS

AT 408 385 B 11/2001
WO 00/66998 A2 11/2000

*Primary Examiner* — Rodney Fuller
(74) *Attorney, Agent, or Firm* — Seed Intellectual Property Law Group LLP

(57) ABSTRACT

A bore imaging system comprises a photodetector configuration and a first bore surface imaging arrangement configured to transmit image light arising from a first image zone on a bore surface to the photodetector. The photodetector configuration comprises a first curved photodetector arrangement which is curved in a plane that is oriented transverse to an axial direction of the bore. The first curved photodetector arrangement comprises a first imaging array that receives image light along a direction transverse to the axial direction.

14 Claims, 5 Drawing Sheets

(56) References Cited

U.S. PATENT DOCUMENTS

| | | | |
|---|---|---|---|
| 9,654,741 B2* | 5/2017 | Baleine | H04N 7/183 |
| 2002/0076178 A1* | 6/2002 | Klocek | A61B 5/015 |
| | | | 385/106 |
| 2004/0247268 A1* | 12/2004 | Ishihara | A61B 5/0062 |
| | | | 385/117 |
| 2004/0249247 A1* | 12/2004 | Iddan | A61B 1/0005 |
| | | | 600/170 |
| 2005/0109918 A1* | 5/2005 | Nikzad | H01L 27/14683 |
| | | | 250/208.1 |
| 2006/0274171 A1* | 12/2006 | Wang | G06K 7/14 |
| | | | 348/294 |
| 2010/0264502 A1 | 10/2010 | Christophersen et al. | |
| 2012/0261551 A1 | 10/2012 | Rogers | |
| 2013/0112881 A1 | 5/2013 | Rudolf | |
| 2014/0276111 A1* | 9/2014 | Gal | A61B 1/00167 |
| | | | 600/478 |
| 2016/0309065 A1* | 10/2016 | Karafin | G02B 6/32 |
| 2017/0097306 A1* | 4/2017 | Ullrich | G01N 21/954 |

* cited by examiner

BORE IMAGING SYSTEM

BACKGROUND

Technical Field

The present application relates generally to bore inspection systems and more particularly to bore imaging systems.

Description of the Related Art

Various bore imaging systems are known that use a bore surface imaging arrangement for imaging the interior of a bore, for example in a cylinder bore of an engine. Exemplary bore inspection systems are disclosed in U.S. Pat. Nos. 4,849,626 (the '626 patent); 7,636,204 (the '204 patent); 8,334,971 (the '971 patent); 8,570,505 (the '505 patent); and U.S. Patent Application No. 2013/0112881, each of which is hereby incorporated herein by reference in its entirety. Such bore imaging systems may be configured to provide a 360 degree view (also referred to as a panoramic view and/or image) of the interior of a bore in order to inspect for form errors or surface defects. Some such systems use high-resolution optics. In any case, such systems may use signal processing to map image pixel signals or detector element signals to coordinates within the interior of the bore. In some such systems, a panoramic image of an approximately annular portion of a bore may be projected onto a two-dimensional (2-D) rectangular imaging array in a circular pattern corresponding to the shape of the annular portion. The circular or annular image pixels may then span a relatively large set of pixels (e.g., most of the rectangular imaging array) while actually imaging onto only a relatively small proportion of that set of pixels (e.g., an annular image pattern within the rectangular imaging array). A typical imaging array must read out each pixel spanned by the circular or annular bore image, even though pixels outside of the annular image pattern (e.g., interior and exterior to it) are not relevant to inspection of the bore. Additionally, such systems may have to utilize image mapping computation to map pixels from the annular image pattern to the surface of the bore. Continuously reading out irrelevant pixels and mapping relevant pixels takes time, which limits the speed with which such a bore imaging system may be used to inspect a bore. Some systems (e.g., as disclosed in the '626 patent) have used fiber optic imaging paths, and routed each fiber to a corresponding photodetector. However, configurations of such systems have also imposed speed limitations, as well as imaging limitations that have limited resolution and/or versatility with regard to the range of bore sizes that may be inspected using a given system.

A high-speed, high-resolution, metrology grade bore imaging system which solves the problems outlined above would be desirable.

BRIEF SUMMARY

A bore imaging system is disclosed that comprises a photodetector configuration and a first bore surface imaging arrangement configured to transmit image light arising from an image zone on a bore surface to the photodetector configuration. The photodetector configuration comprises a first curved photodetector arrangement which is curved in a plane that is oriented transverse to an axial direction of the bore. The first curved photodetector arrangement comprises at least a first imaging array that receives image light along a direction transverse to the axial direction. In various embodiments, such a system provides a high throughput rate for meaningful image data, and a metrology grade imaging configuration that is versatile with regard to measuring a range of bore sizes with high resolution. In various embodiments, the relatively elongated image dimension may cover 360 degrees around the bore. In various embodiments, the features disclosed herein allow the image zone to be scanned axially along the bore at an unprecedented rate without the need for complex image processing to map pixel information.

BRIEF DESCRIPTION OF THE SEVERAL VIEWS OF THE DRAWINGS

The foregoing aspects and many of the attendant advantages will become more readily appreciated as the same become better understood by reference to the following detailed description, when taken in conjunction with the accompanying drawings, wherein.

DETAILED DESCRIPTION

Figure 1:
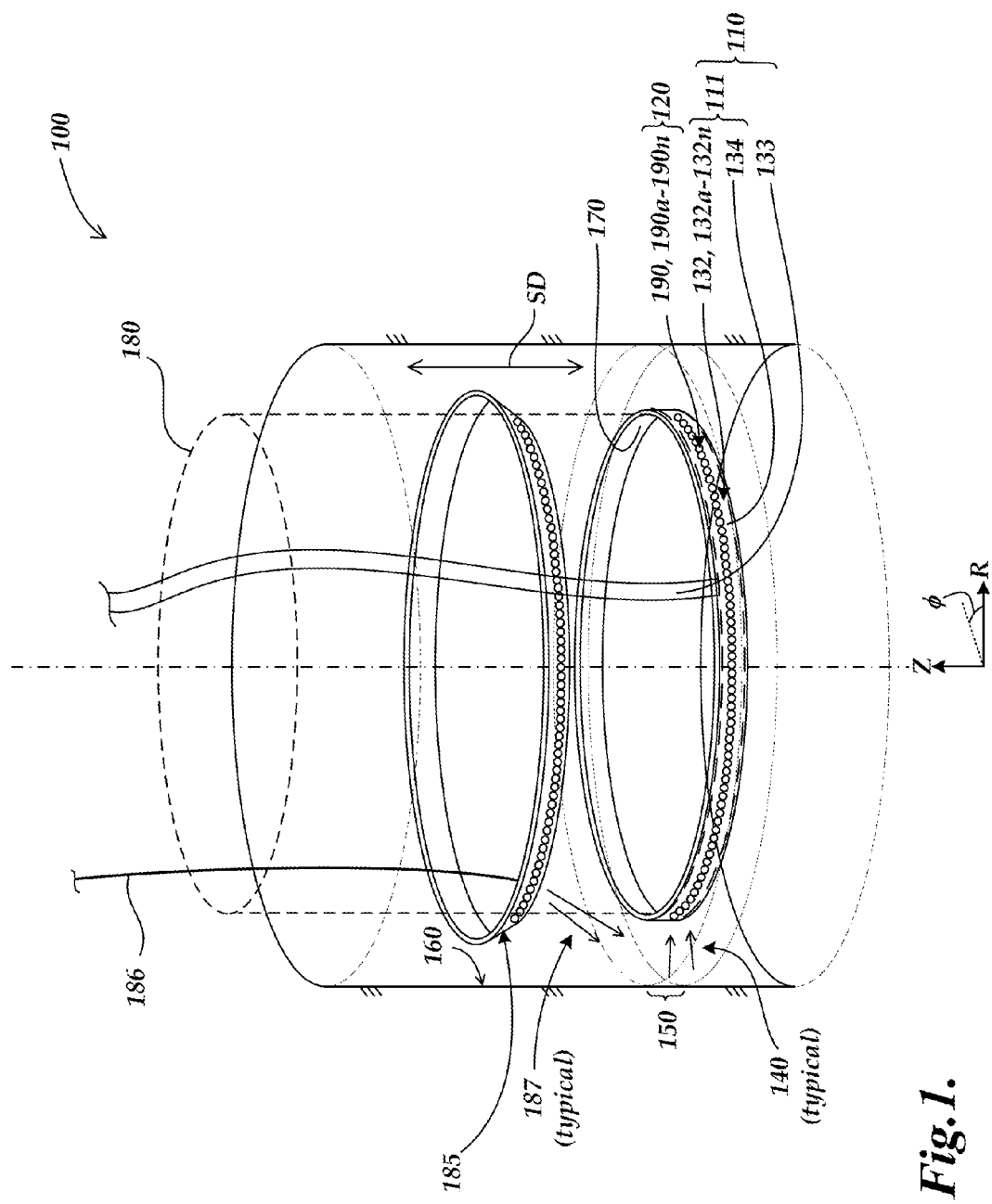
FIG. 1 is a schematic diagram of a first embodiment of a bore imaging system according to principles disclosed herein.

FIG. 1 is a schematic diagram of a first embodiment of a bore imaging system 100 according to principles disclosed herein. In this embodiment, the bore imaging system 100 comprises a photodetector configuration 110 (also referred to herein simply as a photodetector) and a bore surface imaging arrangement 120, carried on a curved carrier 170 that holds them in a stable form. The bore imaging system 100 may be carried on a schematically represented housing member 180 which holds everything in the proper relationship and which may be mounted to or include a motion control system or the like for scanning the bore imaging system 100 along an axial scanning direction SD to image a desired axial section of a bore surface 160. The bore imaging system 100 may further comprise an illumination portion 185, in some embodiments. FIG. 1 is arranged according to cylindrical coordinates Z, R and $\phi$ which are aligned with a cylindrical bore in this example. The photodetector 110 comprises a curved photodetector arrangement 111 which is curved in a plane that is oriented transverse to an axial direction Z of a bore surface 160, as described in greater detail below. The curved photodetector arrangement 111 comprises an imaging array 132 and an array substrate 134. In some embodiments, the imaging array 132 and the array substrate 134 may be merged and/or indistinguishable (e.g., in the form of a semiconductor photodetector array on a thinned semiconductor substrate). In some embodiments, they may be distinguishable elements (e.g., in the form of diced semiconductor photodetector elements bonded to a flexible material that also carries interconnections and the like). In any case, the imaging array 132 comprises photodetector elements 132a-132n (e.g., pixels) that provide image data (e.g., intensity values), which may be output individually, or in parallel, or multiplexed, or serialized, or otherwise processed before being output on connections 133. That is, in some embodiments, processing circuits may be provided as part of the imaging array 132, or on the substrate 134 and/or the carrier 170. In this embodiment, the bore surface imaging arrangement 120 comprises a lens arrangement 190 that images the bore surface 160 onto the curved photodetector arrangement 111. In this embodiment, the lens arrangement 190 takes the form of an array of lens elements 190a-190n, as described in greater detail below with reference to FIG. 2. The illumination portion 185 is connected to an illumination power and control element 186. In alternative embodiments, an illumination portion may be omitted, or provided on the carrier 170, or in any other convenient form.

In operation, the illumination portion 185 is arranged to provide illumination 187 to an image zone 150 on the bore surface 160. The bore surface imaging arrangement 120 is configured to transmit image light 140 arising from the image zone 150 to the photodetector 110, and in particular to the curved photodetector arrangement 111. More specifically, in this particular embodiment, the lens elements 190a-190n of the lens arrangement 190 are configured to transmit image light 140 to photodetector elements 132a-132n of the imaging array 132 along the radial direction R.

In the embodiment shown in FIG. 1, the bore imaging system 100 is moved along a scanning direction SD to provide images that cover the bore surface 160 along an axial direction Z.

In the embodiment shown in FIG. 1, the curved photodetector arrangement 111 is curved in an approximately circular shape on the carrier 170. In some embodiments, the carrier 170 may be a portion of the housing member 180. In various embodiments, the substrate 134 may be a flex print, an elastomer or a thinned semiconductor substrate, or another curvable substrate that provides the required properties for providing a curved imaging array according to principles disclosed herein.

In the embodiment shown in FIG. 1, the bore imaging system 100 is moved along a scanning direction SD to provide images that cover the bore surface 160 along the axial direction Z.

In some embodiments, the curved photodetector arrangement 111 may be provided on a flexible substrate such as a FleX™ Silicon-on-Polymer™ CMOS sensor available from American Semiconductor of Boise, Id., or a curved high-resolution CCD sensor provided by Andanta of Olching, Germany. Various other usable alternatives for fabricating a curved photodetector arrangement are disclosed in U.S. Pat. Nos. 6,791,072; 6,849,843; 7,786,421; 8,372,726; 8,742,325; and U.S. Patent Publications 2010/0264502 and 2012/0261551, all of which are hereby incorporated herein by reference in their entirety.

In some embodiments, the photodetector arrangement 111 may comprise multiple photodetector elements or arrays which are each nominally flat over a limited span, but are arranged along a curved form of the curved photodetector arrangement 111. For example, nominally flat photodetector arrays may be provided on a flexible substrate which is arranged along the curved form of the photodetector arrangement 111. One design consideration in such an embodiment is that each of the photodetector elements should not receive an unacceptably blurred image corresponding to its imaged portion of the image zone 150. Thus, any lens arrangement and cooperating photodetector arrangement should be designed to have complementary curvatures to the extent required to maintain each photodetector or pixel within a desirable image focus depth or range.

In some embodiments, the imaging array 132 may span a relatively narrow dimension along the axial direction Z (e.g., as small as three pixels, or less) and a relatively elongated dimension along the $\phi$ direction (e.g., as many as 5800 pixels).

Figure 2A:
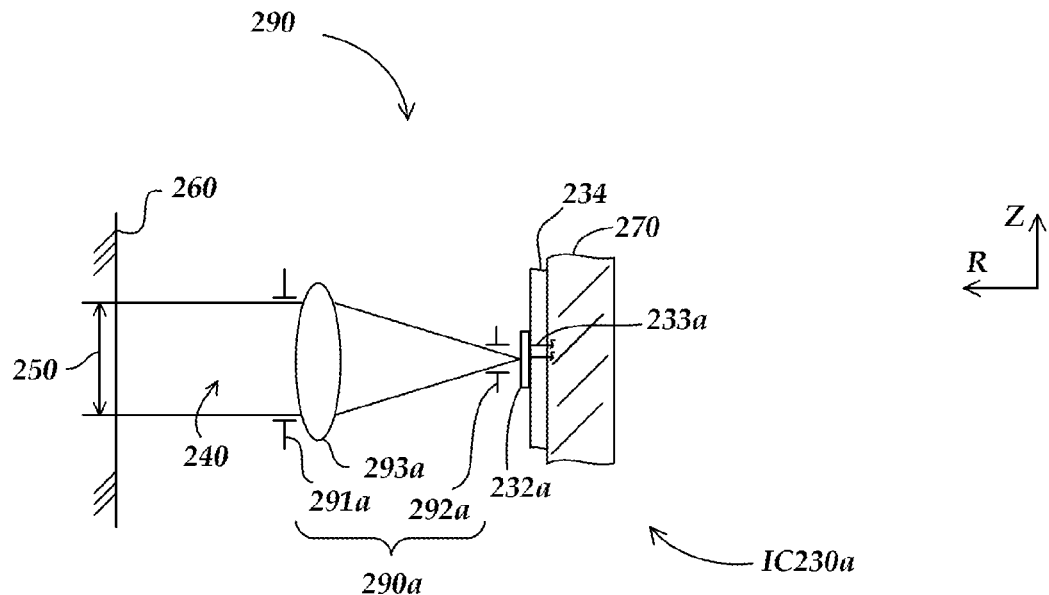
FIGS. 2A and 2B are schematic diagrams of a first embodiment of a lens arrangement usable in a bore imaging system according to principles disclosed herein.
Figure 2B:
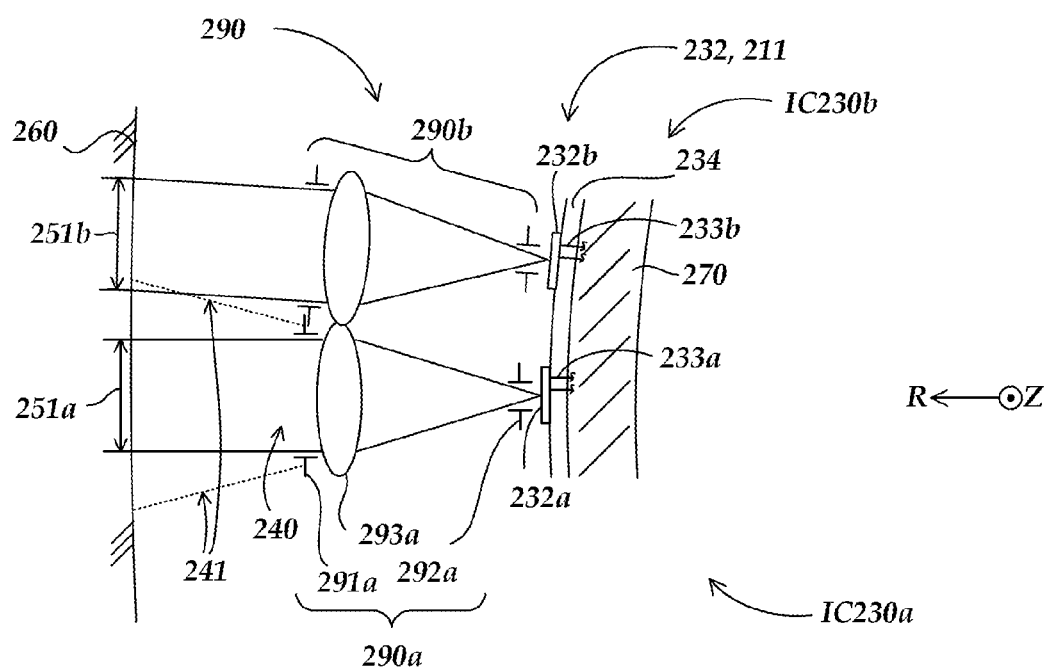

FIGS. 2A and 2B are schematic diagrams of a first embodiment of a lens arrangement 290 usable as the lens arrangement 190 of the bore imaging system 100 shown in FIG. 1. FIG. 2A shows components of one typical image channel IC230a including a respective portion of the lens arrangement 290 that works in cooperation with a respective portion of an imaging array 232. The lens arrangement 290 and the imaging array 232 (e.g., as included in a curved photodetector arrangement 211) comprise a plurality of similar image channels. Many elements numbered 2XX in FIG. 2 may be similar or identical to elements numbered 1XX in FIG. 1, as will be apparent to one of ordinary skill in the art, and may be understood based on previous description or analogy, unless contraindicated.

FIG. 2A shows a view along a direction normal to the R-Z plane of an image channel IC230a, and FIG. 2B shows a top view of two adjacent image channels IC230a and IC230b along a direction parallel to the axial direction Z. The portion of lens arrangement 290 associated with the image channel IC230a is designated 290a and comprises a limiting aperture 291a located in front of a microlens 293a and a limiting aperture 292a located at a back focal plane of the microlens 293a. The portion of lens arrangement 290 associated with the image channel IC230b is designated 290b. The image channel IC230a further comprises a photodetector element 232a. In some embodiments, the photodetector element 232a may comprise a pixel or a small group of pixels. The photodetector element 232a is arranged on (or on part of) a substrate 234 which is attached to a carrier 270. The photodetector element 232a is coupled to a connection 233a which may be understood as an example of an individual instance of the connections 133 of the bore imaging system 100, in one embodiment. The microlens 293a and the apertures 291a and 292a are configured to focus nominally collimated light 240 from an imaging zone 250 of a bore surface 260 into the photodetector element 232a. In some embodiments, the microlens 293a may have a magnification of −1. Conversely, as shown in FIG. 2B, the limiting apertures 291a and 292a are configured to block non-collimated light such as the light rays 241 originating outside a field of view 251 a from entering the image channel IC230a. This prevents light from a region which should nominally be imaged by an adjacent photodetector element (e.g., from a region in the field of view 251b of the image channel IC230b) from being input by the photodetector element 232a, and therefore suppresses "image cross talk" between adjacent photodetector elements. This may be understood to improve the lateral image resolution of the system. The adjacent image channel IC230b is similarly configured as the image channel IC230a described above, and includes a photodetector element 232b coupled to a connection 233b. It will also be appreciated that such a lens arrangement also enhances the depth of field, allowing metrology grade imaging of a range of bore sizes.

Figure 3:
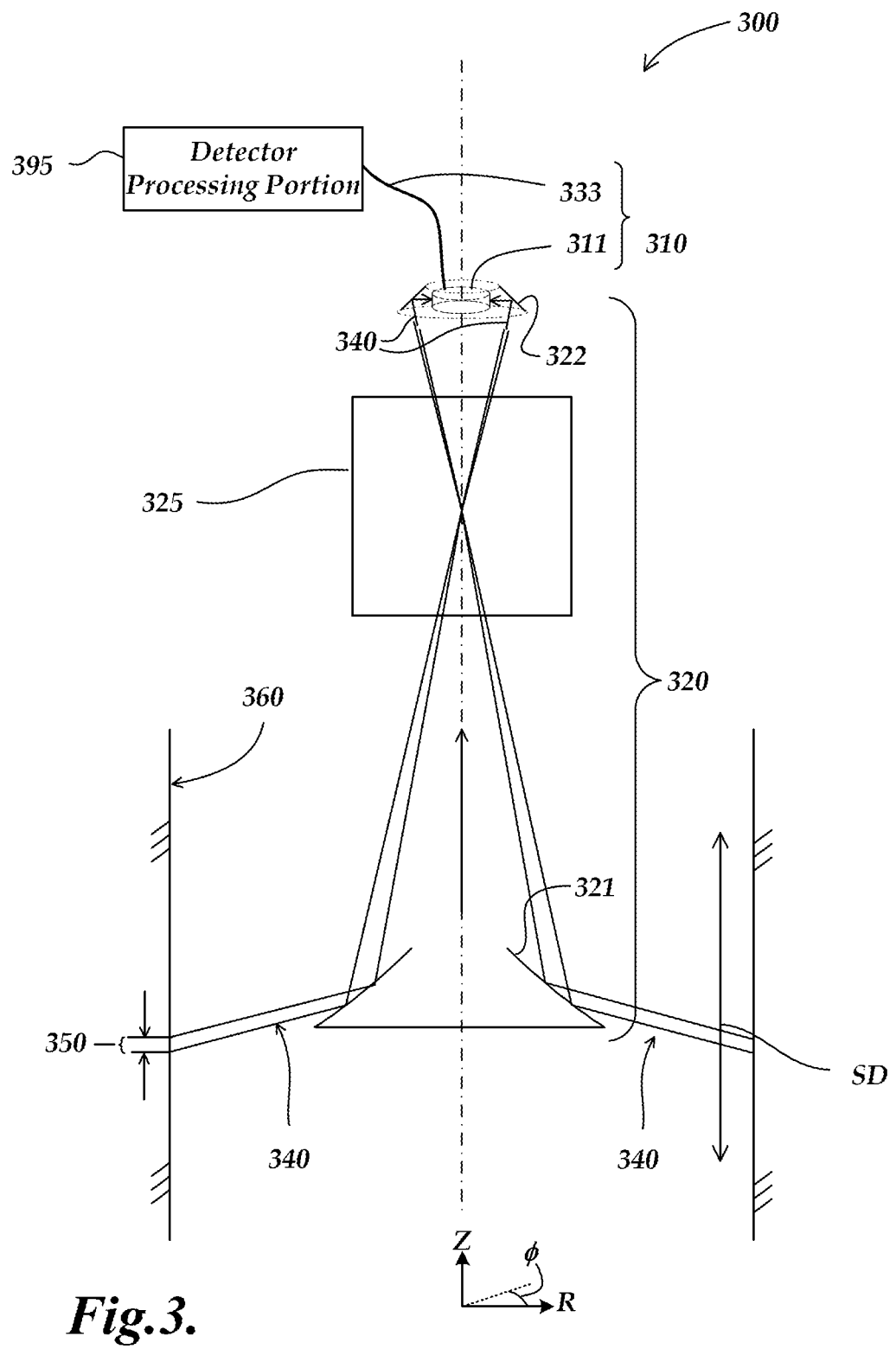
FIG. 3 is a schematic diagram of a second embodiment of a bore imaging system according to principles disclosed herein.

FIG. 3 is a schematic diagram of a second embodiment of a bore imaging system 300 according to principles disclosed herein. Many elements numbered 3XX in FIG. 3 may be analogous to or similar to elements numbered 1XX in FIG. 1 (e.g., 311 is analogous to 111), as will be apparent to one of ordinary skill in the art, and may be understood based on previous description or analogy, unless contraindicated. In some cases size or form may be different, but function, fabrication or purpose may be similar, as will be understood by one of ordinary skill in the art based on this disclosure.

The bore imaging system 300 comprises a photodetector 310, and a bore surface imaging arrangement 320. In some embodiments, the bore imaging system 300 may include an illumination portion (e.g., analogous to the illumination system 190 shown in FIG. 1), not shown. The bore imaging systems may be arranged on a housing member or frame, not shown, which holds everything in the proper relationship and which may be mounted to or include a motion control system or the like for scanning the bore imaging system 300, and/or adjusting its imaging direction, along an axial scanning direction SD. FIG. 3 is arranged according to cylindrical coordinates Z, R and φ which are aligned with a cylindrical bore in this example. The photodetector 310 comprises a curved photodetector arrangement 311 which is curved in a plane that is oriented transverse to an axial direction Z of a bore surface 360, as described in greater detail below. The curved photodetector arrangement 311 may be understood to be analogous to the photodetector arrangement 111, and may be similarly fabricated, that is, comprising an imaging array and a substrate, as previously outlined. The imaging array generally comprises photodetector elements which are coupled to connections 333 which are configured to output image data to a detector processing portion 395, as previously outlined. The image data may be processed image data in some embodiments. The bore surface imaging arrangement 320 is significantly different in form from the bore surface imaging arrangement 120 shown in FIG. 1. In particular, the bore surface imaging arrangement 320 comprises a panoramic imaging arrangement comprising a first reflector element 321 that reflects around 360 azimuth degrees, a lens arrangement 325, and a second reflector element 322 that reflects around 360 azimuth degrees, all located along an optical path between the image zone 350 and the photodetector 310.

In operation, the bore surface imaging arrangement 320 is configured to transmit image light 340 arising from the image zone 350 on the bore surface 360 to the photodetector 310, and in particular to the photodetector elements of its imaging array.

More specifically, the first reflector element 321 is arranged to receive image light 340 that arises from the image zone 350, along a direction transverse to the axial direction Z (e.g., approximately along the radial direction R), deflect it, and output it to the lens arrangement 325 generally along the direction of the bore axis (e.g., the Z direction.) The lens arrangement 325 is configured to transmit the image light 340 to the second reflector element 322, generally along the direction of the bore axis (e.g., the Z direction) with a desired magnification. The lens arrangement 325, or more generally the bore surface imaging arrangement 320, may further include various limiting apertures or the like, which may include an annular aperture arrangement in some embodiments, in order to enhance the field of view selection, depth of field, and/or resolution of the bore imaging system 300 when imaging the image zone 350. The second reflector element 322 is arranged to receive the image light 340 from lens arrangement 325, deflect it, and transmit the image light 340 to the curved photodetector arrangement 311 of photodetector 310 along a direction transverse to the axial direction Z (e.g., approximately along the radial direction R). The curved photodetector arrangement 311 is arranged to receive that image light 340.

In the particular embodiment shown in FIG. 3, the lens arrangement 325 is configured to demagnify the image light 340 and transmit it to the second reflector element 322, which deflects the light approximately along an inward radial direction to a compact curved photodetector arrangement 311, which has detector elements that face approximately along an outward radial direction. Such a configuration may allow a very compact curved photodetector arrangement 311 in some embodiments, and/or may have the advantage of inherently concentrating the inward radially converging image light 340 to provide better image intensity and/or resolution at the photodetector elements of the curved photodetector arrangement 311.

In the embodiment shown in FIG. 3, the first reflector element 321 and the second reflector element 322 appear to have an approximately conical shape. However, it should be appreciated that different shapes of reflector elements may be utilized, for example, to improve image distortions or enhance imaging resolution.

In some embodiments, during operation, the bore imaging system 300 is moved along a scanning direction SD to provide images that cover the bore along the axial direction. In alternative embodiments, the bore surface imaging arrangement 320 may comprise image path adjustment elements comprising deformable and/or coordinated movable imaging elements that deflect the field of view and focus of the system axially along the bore without having to move the entire bore surface imaging arrangement 320 along the scanning direction SD to do so. Such a system may provide faster scanning speed or mechanical response time for relocating the image zone 350. Using modern optical design simulation software and/or ray tracing programs, various configurations for such a system may be realized by one of ordinary skill in the art of optical design.

Figure 4:
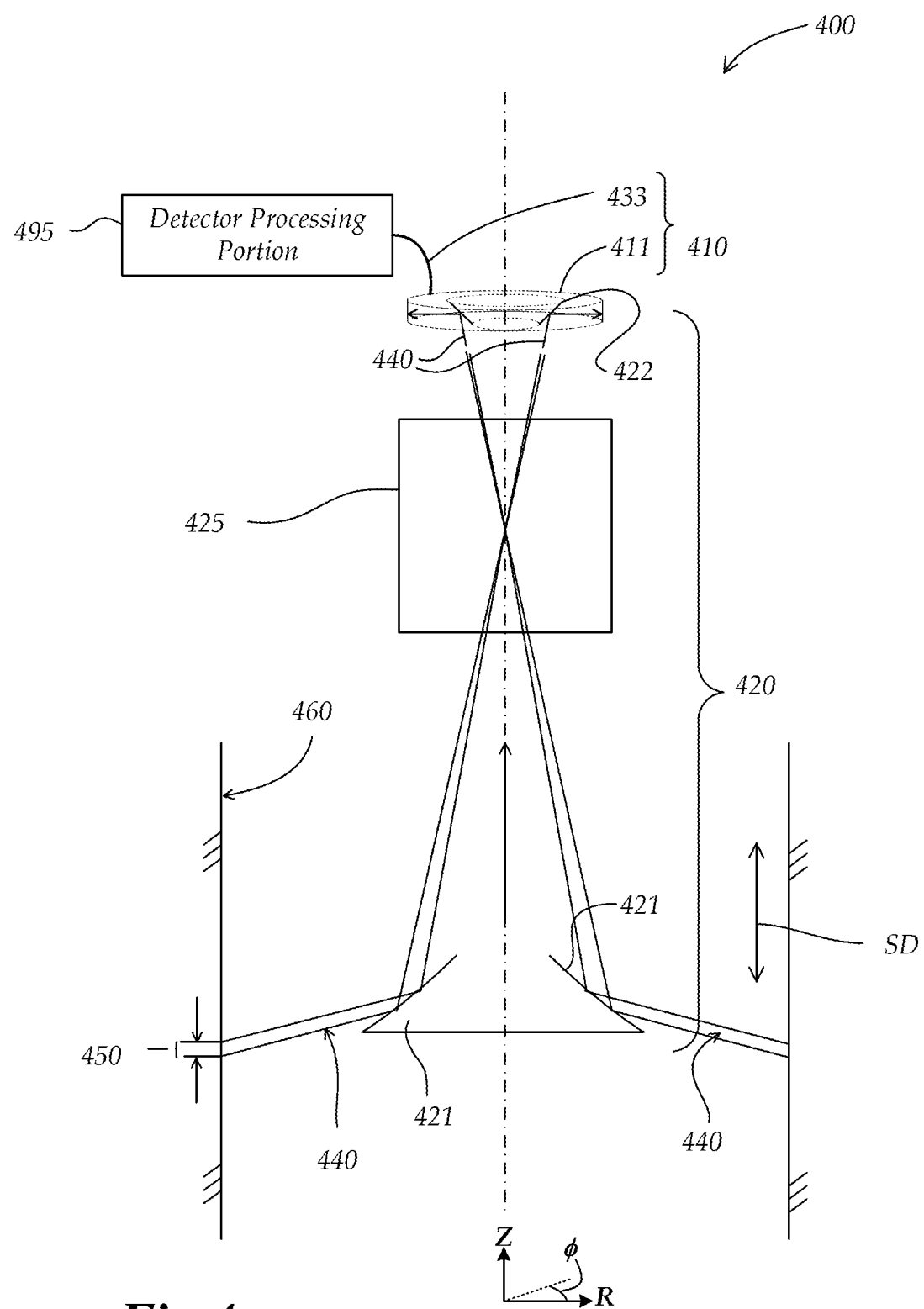
FIG. 4 is a schematic diagram of a third embodiment of a bore imaging system according to principles disclosed herein.

FIG. 4 is a schematic diagram of a third embodiment of a bore imaging system 400 according to principles disclosed herein. Many elements numbered 4XX in FIG. 4 may be analogous or identical to elements numbered 3XX in FIG. 3 (e.g., 421 may be similar or identical to 321 in some embodiments), as will be apparent to one of ordinary skill in the art, and may be understood based on previous description or analogy, unless contraindicated. In some cases size or form may be different, but function, fabrication or purpose may be similar, as will be understood by one of ordinary skill in the art based on this disclosure.

The bore imaging system 400 comprises a photodetector 410, and a bore surface imaging arrangement 420, all of which may be understood based on description of the bore imaging system 300, outlined with reference to FIG. 3, above. The only significant difference between the bore imaging system 400 and the bore imaging system 300 is that in the bore surface imaging arrangement 420 the second reflector element 422 is configured to deflect the image light 440 approximately along an outward radial direction to a curved photodetector arrangement 411, which has detector elements that face approximately along an inward radial direction. Such a configuration may allow a less curved photodetector arrangement 411 in some embodiments (e.g., for use in embodiments wherein the photodetector elements reside on a substrate that cannot be curved with a small bend radius, in contrast to the curved photodetector arrangement 311), and/or may have the advantage of allowing more photodetector elements of a given size to be used per angular increment of the curved photodetector arrangement 411, to improve the spatial image sampling and/or resolution in the bore imaging system 400.

Figure 5:
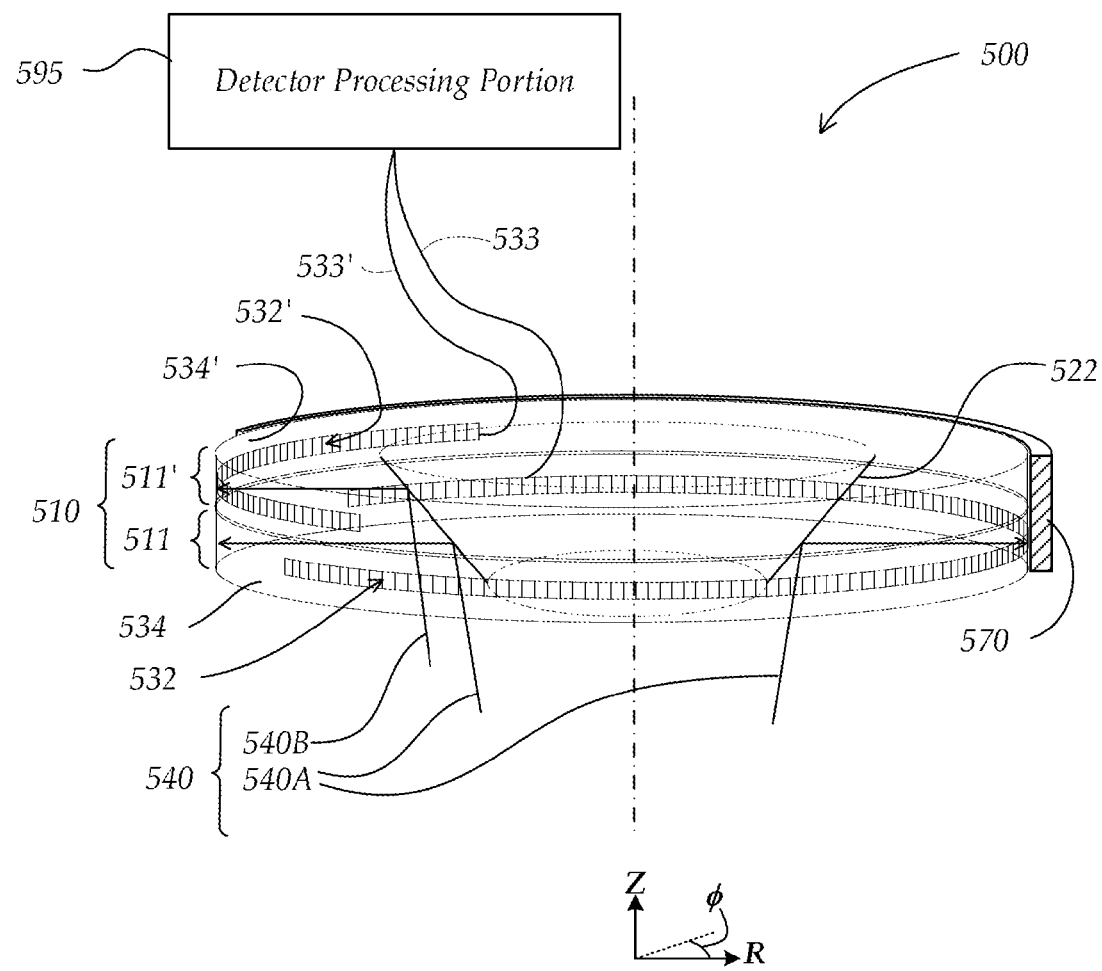
FIG. 5 is a schematic diagram of an embodiment of a photodetector usable in various embodiments of a bore imaging system according to principles disclosed herein, wherein the photodetector comprises first and second curved photodetector arrangements.

FIG. 5 is a schematic diagram 500 including an embodiment of a photodetector 510 usable in various embodiments of a bore imaging system according to principles disclosed herein (e.g., the bore imaging system 400 outlined above with reference to FIG. 4). For example, the photodetector 510 may be used in place of the photodetector 410 shown in FIG. 4. Many elements numbered 5XX in FIG. 5 may be analogous or similar to elements numbered 4XX in FIG. 4 and/or 2XX in FIG. 2, as will be apparent to one of ordinary skill in the art, and may be understood based on previous description or analogy, unless contraindicated.

The primary difference between the photodetector 510 and the photodetector 410 shown in FIG. 4 is that the photodetector 510 comprises a first curved photodetector arrangement 511 and a second curved photodetector arrangement 511', which are curved in planes that are oriented transverse to an axial direction Z of a bore surface, and axially offset from one another. The first curved photodetector arrangement 511 comprises an imaging array 532 on a substrate 534 and the second curved photodetector arrangement 511' comprises an imaging array 532' on a substrate 534' that each receive respective portions 540A and 540B of image light 540 that have been deflected along a direction transverse to the axial direction Z (i.e., along the radial direction R) by the second reflector element 522. It will be understood that the dimensions shown for various elements and/or their separation along the Z direction in FIG. 5 have been exaggerated for purposes of illustration. In some embodiments, the dimensions shown for various elements and/or their separation along the Z direction are minimized as much as possible, to provide a more compact imaging system.

The substrates 534 and 534' are mounted to a circular carrier 570 (partially shown, in cutaway view). It will be appreciated that in some embodiments the substrates 534 and 534' may comprise portions of a single element. The first and second curved photodetector arrangements 511 and 511' may generally be fabricated according to any of the methods previously outlined and/or referenced herein. The imaging arrays 532 and 532' may comprise schematically represented individual photodetector elements which are coupled to respective connections 533 and 533' configured to output image data to a detector processing portion 595. In some embodiments, the detector processing portion 595 may be provided as part of the imaging arrays 532 and 532', or on the substrates 134 and/or 134' and/or the carrier 170.

One reason for providing the first and second curved photodetector arrangements 511 and 511' may be that assembly considerations, and/or connections or conductors associated with an imaging array, may make it uneconomical, or inconvenient to assemble a single curved photodetector that does not have a gap between photodetector elements somewhere along, or at the end of, the array. In particular, full density 360-degree photodetector element coverage may be difficult or expensive to provide in a single plane transverse to the Z axis. In such a case, at any azimuth angle ϕ at which there is a gap in the photodetector element coverage of a first curved photodetector arrangement 511, there may be photodetector element coverage provided at the same azimuth angle, in a second curved photodetector arrangement 511', with an axial direction offset from the curved photodetector arrangement 511. In such a configuration, the portion of an image zone (e.g., the image zone 450) that is imaged by each of the first and second curved photodetector arrangements 511 and 511' is different (e.g., each images a different axial coordinate in the image zone). However, as a bore imaging system is scanned along the axial direction, complete imaging at all azimuth angles may be obtained by a combination of the image data from the first and second curved photodetector arrangements 511 and 511'. In some embodiments, there may be redundant data obtained at some azimuth angles (e.g., as would be the case with the photodetector 510). In such a case, the extra data may be used for various purposes or simply ignored in various embodiments.

Another reason for providing first and second curved photodetector arrangements, when fabrication of an imaging array or arrays leaves no gaps at any azimuth angle, may be simply to provide redundant image data during a single scan. This may be used to provide more reliable imaging, or allow faster processing or scanning, or for various other reasons in various embodiments. Another reason for providing first and second curved photodetector arrangements may be simply to provide image only desired azimuthal arc segments that are of interest in a particular bore wall inspection application. Each curved photodetector may be sized and located to match its respective desired azimuthal arc segment along the bore wall. This may limit the data acquisition and processing time, and allow a higher axial scanning rate in some specific applications.

It will be appreciated that in other embodiments, if a long enough imaging array can fabricated, it may be wound on a carrier, e.g., in a helix, or to overlap a portion of itself, to form a single curved photodetector arrangement that avoids or covers all potential photodetector gaps over 360 degrees of azimuth angle, in a manner analogous to that outlined above.

It should be appreciated that some embodiments of a bore imaging system according to the principles disclosed herein may comprise a second complete photodetector and bore surface imaging arrangement. In one such application, the second photodetector and bore surface imaging arrangement may be arranged to image a second image zone offset from a first image zone in the axial direction Z in order to cut down the time required to scan a given axial segment of a bore surface. Image data from the first photodetector and the second photodetector may be stitched to form a full image of the bore surface. In another such embodiment, the second photodetector and bore surface imaging arrangement may be arranged to image the same image zone as a first photodetector and bore surface imaging arrangement, but along a different optical path with a different angle with respect to the first image zone than the first bore surface imaging arrangement. Such a bore imaging system may be capable of three-dimensional imaging of a bore surface.

While various embodiments have been illustrated and described, numerous variations in the illustrated and described arrangements of features and sequences of operations will be apparent to one skilled in the art based on this disclosure. Thus, it will be appreciated that various changes can be made therein without departing from the spirit and scope of the invention.

The embodiments of the invention in which an exclusive property or privilege is claimed are defined as follows:

1. A bore imaging system comprising:
a photodetector configuration; and
a first bore surface imaging arrangement configured to transmit image light arising from a first image zone on a bore surface to the photodetector configuration,
wherein:
the photodetector configuration comprises a first curved photodetector arrangement which is curved in a plane that is oriented transverse to an axial direction of the bore; and the first curved photodetector arrangement comprises at least a first imaging array that receives image light along a direction transverse to the axial direction.

2. The bore imaging system of claim 1, wherein the first curved photodetector arrangement is curved in an approximately circular curve.

3. The bore imaging system of claim 1, wherein:
the first bore surface imaging arrangement comprises:
a first reflector element, and
a second reflector element located along an optical path between the first reflector element and the photodetector configuration; and
the first reflector element is arranged to receive image light that arises from the first image zone on the bore surface approximately along a radial direction and output it to the second reflector element approximately along the axial direction; and
the second reflector element is arranged to receive image light from the first reflector element and transmit the image light to the photodetector configuration along the radial direction.

4. The bore imaging system of claim 3, wherein the first reflector element and the second reflector element are panoramic reflector elements that reflect around 360 azimuth degrees.

5. The bore imaging system of claim 1, wherein the photodetector configuration is arranged to detect light over a range of 360 azimuth degrees along the direction transverse to the axial direction.

6. The bore imaging system of claim 1, wherein the photodetector configuration comprises a plurality of curved photodetector arrangements.

7. The bore imaging system of claim 6, wherein:
the first curved photodetector arrangement and a second curved photodetector arrangement are offset from each other along the axial direction; and
at least a first portion of the first imaging array of the first curved photodetector arrangement is aligned along the axial direction of the bore to overlap or align with an azimuth angle imaging gap that is not covered by photodetector elements included in an imaging array of the second curved photodetector arrangement.

8. The bore imaging system of claim 1, wherein the first curved photodetector arrangement is located on a flexible substrate which forms a helix or overlaps a portion of itself along an azimuthal angular arc segment of more than 360 degrees.

9. The bore imaging system of claim 1, wherein the first curved photodetector arrangement is located on a concave surface facing inward in a radial direction.

10. The bore imaging system of claim 1, wherein the first curved photodetector arrangement is located on a convex surface facing outward in a radial direction.

11. The bore imaging system of claim 1, wherein the first bore surface imaging arrangement further comprises a lens arrangement configured to focus light arising from the bore surface along an optical path of the first bore surface imaging arrangement.

12. The bore imaging system of claim 1, further comprising a second photodetector configuration and a second bore surface imaging arrangement.

13. The bore imaging system of claim 12, wherein the second bore surface imaging arrangement is configured to transmit image light arising from a second image zone on the bore surface to the second photodetector configuration.

14. The bore imaging system of claim 12, wherein the second bore surface imaging arrangement is configured to transmit image light arising from the first image zone to the second photodetector configuration along an optical path with a different angle with respect to the first image zone than the first bore surface imaging arrangement.

* * * * *